US007547527B2

(12) United States Patent
Baur et al.

(10) Patent No.: US 7,547,527 B2
(45) Date of Patent: Jun. 16, 2009

(54) USE OF PROBIOTIC LACTIC ACID BACTERIA FOR BALANCING THE SKIN'S IMMUNE SYSTEM

(76) Inventors: Markus Baur, Maienweg 100, Ulm (DE) 89081; Lionel Breton, 14 Rue Satory, F-78000 Versailles (FR); Francois Couzy, Route Monts de Lavaux 498, 1090 La Croix /Lutry (CH); Audrey Gueniche, 4 Rue Louis de Broglie, F-92500 Rueil Malmaison (FR)

( * ) Notice: Subject to any disclaimer, the term of this patent is extended or adjusted under 35 U.S.C. 154(b) by 0 days.

(21) Appl. No.: 10/381,911

(22) PCT Filed: Oct. 4, 2001

(86) PCT No.: PCT/EP01/11475

§ 371 (c)(1),
(2), (4) Date: Aug. 12, 2003

(87) PCT Pub. No.: WO02/28402

PCT Pub. Date: Apr. 11, 2002

(65) Prior Publication Data

US 2004/0013706 A1    Jan. 22, 2004

(30) Foreign Application Priority Data

Oct. 6, 2000   (EP)   .................. 00121865

(51) Int. Cl.
| | |
|---|---|
| *C12P 1/00* | (2006.01) |
| *A61K 39/02* | (2006.01) |
| *A61K 39/116* | (2006.01) |
| *A61K 39/38* | (2006.01) |
| *A61K 8/49* | (2006.01) |
| *G01N 31/00* | (2006.01) |
| *G01N 33/04* | (2006.01) |

(52) U.S. Cl. .................. 435/41; 424/234.1; 424/203.1; 424/184.1; 424/70.9; 436/20; 436/22

(58) Field of Classification Search .............. 424/184.1, 424/234.1, 59
See application file for complete search history.

(56) References Cited

U.S. PATENT DOCUMENTS

| | | | |
|---|---|---|---|
| 5,302,389 A | | 4/1994 | Kripke et al. |
| 6,488,970 B1 * | | 12/2002 | Hora ............................ 426/72 |
| 6,645,506 B1 * | | 11/2003 | Farmer ..................... 424/260.1 |

FOREIGN PATENT DOCUMENTS

| | | | |
|---|---|---|---|
| FR | 2 682 596 | | 4/1993 |
| FR | 2 718 752 | | 10/1995 |
| JP | 09002959 | | 1/1997 |
| WO | WO 97/00078 | * | 1/1997 |
| WO | WO 99 17788 | * | 4/1999 |
| WO | WO 99/17788 | * | 4/1999 |
| WO | WO 00/35465 | | 6/2000 |
| WO | WO 00/41707 | | 7/2000 |

OTHER PUBLICATIONS

Isolauri, E. et al. 2000. Probiotics in the management of atopic eczema. Clinical and Experimental Allergy. v30: 1604-1610.*
Majamaa et al (Journal of Allergy and Clinical Immunology, 1997, vol. 99, No. 2, p. 179-185).*
Natarajan et al (Mutation Research, 1988, 206/1, 47-54).*
Isolauri et al (Clinical and Experimental Allergy, 2000, vol. 30, pp. 1604-1610.*
Reeve et al (Sunscreens and Immunosuppression by UVR, vol. 97, No. 4, Oct. 1991).*
Ahsan et al (Photochem Photobiol, Jul.-Aug. 2007;83(4):986-93). (Abstract only).*
Natarajan et al (Mutation Research) 206 (1988) 47-54))(Abstract only).*
McCarthy et al (Nutr Cancer, 1997;27(3):231-7) (Abstract only).*
Isolauri et al (Clinical and Experimental Allergy, 2000, vol. 30, pp. 1604-1610).*
Kotaro abstract entitled "Immuno-globulin E antibody production suppressant and antiallergic agent" XP-002163508.
Isolauri et al. article entitled "Probiotics in the management of atopic eczema" *Clinical and Experimental Allergy*, (2000), vol. 30, pp. 1604-1610.
Bergstresser et al., "Sensitization and Elicitation of Inflammation in Contact Dermatitis", Immunology vol. 46, pp. 219-245 (1989).
Reeve et al., ": The protective effect of indomethacin on photocarcinogenesis in hairless mice", Cancer Letters vol. 95, pp. 213-219 (1995).
Reeve et al., "Differential Protection by Two Sunscreens from UV Radiation—Induced Immunosuppression", The Journal of Investigative Dermatology vol. 97, pp. 624-628, (1991).
R. Fuller, "Probiotics in man and animals", Journal of Applied Bacteriology vol. 66, pp. 365-378 (1989).
Schiffrin et al., "Immune modulation of blood leukocytes in humans by lactic acid bacteria: criteria for strain selection", American Journal for Clinical Nutritionists vol. 66, pp. 515-520 (1997).
Peguet et al., "Effects of chronic sunlight exposure on the immunological function of the human epidermis", British Journal of Dermatology vol. 133, pp. 660-661 (1995).

* cited by examiner

*Primary Examiner*—Robert B. Mondesi
*Assistant Examiner*—Vanessa L. Ford
(74) *Attorney, Agent, or Firm*—K & L Gates LLP

(57) ABSTRACT

The present invention pertains to the use of probiotics for the preparation of a carrier for balancing the skin's immune function. In particular, the present invention pertains to the use of probiotic micro-organisms for balancing the skin's immune function under stress conditions, such as a exposure to ultraviolet radiation, specifically for enhancing the skin's immune activity and reducing the tendency to develop allergic reactions under such conditions.

8 Claims, 6 Drawing Sheets

USE OF PROBIOTIC LACTIC ACID BACTERIA FOR BALANCING THE SKIN'S IMMUNE SYSTEM

The present invention pertains to the use of probiotics for the preparation of a carrier for balancing the skin's immune function. In particular, the present invention pertains to the use of probiotic micro-organisms for improving the skin's immune function under stress conditions, leading to immune suppression, specifically for normalizing the skin's immune activity and reducing the tendency to develop hyper-reactions under such conditions.

The continuous decrease of the atmosphere's ozone layer with the concurrent increase of ultraviolet radiation reaching the planet's surface has attracted a great deal of interest in its potential consequence on human health. Although exposure to ultraviolet radiation is needed for humans to produce vitamin D, growing evidence suggests that extensive exposure to sun-light, in particular to ultraviolet radiation, causes a variety of problems in the skin, including induction of certain skin cancers and induction of accelerated skin ageing (photoageing).

It is presently hypothesized that the primary factor of generating skin cancer is a mutational damage in the DNA of the generative cells in the skin caused by ultraviolet radiation while UV-light induced injury to the skin's immune system obviously seems to supply a second factor necessary for the further development thereof In a healthy system early malignant cells are eliminated by the normal functioning of the skin's immune system. Yet, upon ultraviolet radiation the skin's immune system seems to undergo suppression and cannot perform its usual surveillance function any more. As a consequence very early skin cancer cells are not eliminated, which situation will eventually lead to the malignant cells to escape the immune system and develop to tumours.

In addition to these established health concerns, research has also provided evidence suggesting that exposure to ultraviolet radiation may negatively affect a variety of immune responses in living beings both locally, within the UV-irradiated skin, and also systemically, i.e. at sites distant from the irradiated skin. Exposure of mice to UV-B radiation has been found to interfere with the reaction of UV-induced skin cancers and the induction of delayed type and contact hypersensitivity (DTH, CHS) responses initiated at unirradiated sites. These forms of immuno-suppression found upon ultraviolet radiation are considered to be associated with the induction of antigen-specific suppressor T-lymphocytes. The DTH response is particularly important because this T-lymphocyte-mediated immune reaction is responsible for protection against many chronic infectious diseases.

Current experimental evidence implicates soluble substances derived from UV-irradiated keratinocytes as probable mediators of UV-induced systemic suppression of DTH- and CHS-responses. Based on an in vivo action spectrum for systemic suppression of CHS in mice, it has been proposed that urocanic acid, a deamination product of histidine, present in the stratum corneum, is one of the photoreceptor for this form of UV-induced immuno-suppression.

Apart from suppressing the skin's immune system ultraviolet radiation has been found to also induce inflammatory and irritant effects in the skin, which may eventually result in the development of erythema, edema and/or flaking or scaling (hyperkeratosis) of the skin. These inflammatory and/or irritant reactions are quite separate and dissociable from the first mentioned one, in that in contrast to the suppression of the immune system these reactions are rather related to a stimulation thereof.

In the art there have been several attempts to alleviate the detrimental effects of ultraviolet radiation on the skin, such as by using sunscreens or other particular pharmacological agents.

In J. Invest. Dermatol., 97 (1991), 624-628 it is reported that topical application of ultraviolet radiation-absorbing compounds (sunscreens) is effective in preventing ultraviolet radiation-induced erythema and edema but cannot prevent UV-light induced immuno-suppression This finding was confirmed by several other studies, according to which sunscreens seem to prevent inflammation and/or irritation but do not provide complete prophylactic protection against the immuno-suppressive effects of ultraviolet radiation.

Furthermore, known pharmacological agents which are commonly employed for the treatment of irritated and inflamed skin, such as corticosteroids, indomethiacin or acetylsalicylic acid were found to be without effect in treating the UV-light induced suppressed condition of the skin's immune system when they are applied after the injury is manifest. As proposed by Bergstresser et al. in Immunology 46 (1989), 219-245, local application of corticosteroids reduce the skin's immune response in general. Although indomethacin has been demonstrated by Reeve et al., in Cancer Letters 95 (1995), 213-219 to inhibit photo-carcinogenesis this effect appears to involve both the initiation period and the promotion period of tumour development and thus is thought to be a function of a generalized anti-carcinogenesis effect rather than an effect on the skin immune system. Thus, there appears to be a pattern whereby agents capable of suppressing inflammation and irritancy may not protect the skin's immune system.

On the other hand agents that proved to be effective against ultraviolet radiation induced immuno-suppression did not show any effect in improving inflammatory and irritant effects caused by the skin's exposure to ultraviolet radiation. In U.S. Pat. No. 5,302,389 such an agent and a method for the treatment or prevention of UV-induced immuno-suppression through the application of liposome-encapsulated DNA repair enzymes is proposed. This agent is, however, not effective for treating inflammatory and irritant responses of the skin.

Consequently, there is a need in the art for an agent that may reduce the skin's tendency to develop hyper-reactions when being subjected to stress conditions, and which is capable to reduce the effect of ultraviolet radiation on suppressing the skin's immune system.

SUMMARY OF THE INVENTION

In the past various publications described micro-organisms exerting a beneficial influence on the individual's well being. According to R. Fuller in the Journal of Applied Bacteriology 66 (1989), 365-378, these micro-organisms were designated "probiotics" and were defined as live microbes beneficially affecting the host by improving its intestinal microbial balance.

Probiotics are non-pathogenic and non-toxigenic organisms, that survive passage through the stomach and small intestine. Upon continuous ingestion by the host they eventually may colonize the gut to a substantial extent thus competing with other potentially pathogenic bacteria for nutrients and/or attachment sites on the gastro-intestinal wall and reducing their numbers and reducing or preventing infections.

Until now a number of different probiotic micro-organisms have been found, which all are reported to exert their effect in the gut via the production of toxins, metabolic by-products, short chain fatty acids and the like.

It has also been demonstrated that the microbiota of the gastrointestal tract may affect the mucosal immunity within the host According to Schiffin et al., in Am. J. Clin. Nutr. 66 (1997), 520, the intestinal epithelial cells, blood leukocytes, B- and T-lymphocytes, and also accessory cells of the immune system have all been implicated in the aforementioned immunity to a certain extent. Accordingly, probiotic organisms are considered to interact with the immune system at many levels including cytokine production, mononuclear cell proliferation, macrophage phagocytosis and killing, immunity to bacterial and protozoan pathogens, and the like.

Since the biological activity of the probiotics is mainly taking place in/on the gut's mucosa or the adjacent tissue of the individual, the effect of such micro-organisms was considered to reside mainly in this part of the body. In this respect, literature provided ample evidence that ingestion of probiotics by an individual may show some effect in the gastro-intestial tract. WO 00/41707 discloses a Lactobacillus salivarius strain useful in the prophylaxis or treatment of undesirable gastrointestinal inflammatory activity such as inflammatory bowel disease or irritable bowel syndrome. Further, in WO 00/35465 compositions for the oral administration of Lactobacillus and/or other probiotic organisms are disclosed, for establishment and maintenance of a healthy urogenital flora.

During the extensive studies leading to the present invention it was now surprisingly found that probiotics do also exert an effect in an individual's body at a location distant from the region in which they colonize it. In particular, it has been found that probiotic micro-organisms do also exert an activity on the immune system in the skin of the individual. Accordingly it has been found that upon ingestion by an individual they may balance a suppression of the skin's immune system inherent to exposure to stress, such as physical, chemical or biological stress, while they may also reduce the individual's tendency to develop inflammatory and/or irritant reactions upon exposure to such a stress condition.

Consequently, according to the broadest aspect the present invention provides for the use of probiotics or a culture supernatant thereof for the preparation of a carrier for balancing the skin's immune function.

For the purpose of the present invention the term "balancing the skin's immune function" shall be interpreted as normalizing the immune function under a stress condition, that leads to a suppression of the immune system, that is, maintaining an immune function or immune condition at a level normally prevailing in the skin even when being exposed to such stress conditions. A stress condition shall be interpreted to comprise physical stress, e.g. ultraviolet irradiation of the skin, chemical stress, such as exposure to chemical agents, or allergenic material, or biological stress, such as being exposed to or infected by micro-organisms, such as pathogenic bacteria, viruses, fungi etc. Under such conditions the immune system is on one hand suppressed, e.g. when being exposed to irradiation with UV-light, and on the other hand over-stimulated, such as when being exposed to irritants and allergens. Further, in the context of this invention culture supernatant thereof shall designate the supernatant of a culture of a probiotic as such or in concentrated form or the active metabolite(s) isolated therefrom.

It has now been found that in case of administering probiotics to an individual, which may colonize the individual's gut, or a culture supernatant thereof, the immuno-suppressive effect of certain stress conditions, such as e.g. ultraviolet radiation, is found to be less pronounced or substantially reduced, while inflammatory and/or irritant reactions do occur only to a diminish degree or not at all.

Additional features and advantages of the present invention are described in, and will be apparent from, the detailed description of the presently preferred embodiments and the drawings.

BRIEF DESCRIPTION OF THE FIGURES

In the figures.

DETAILED DESCRIPTION OF THE INVENTION

Figure 1:
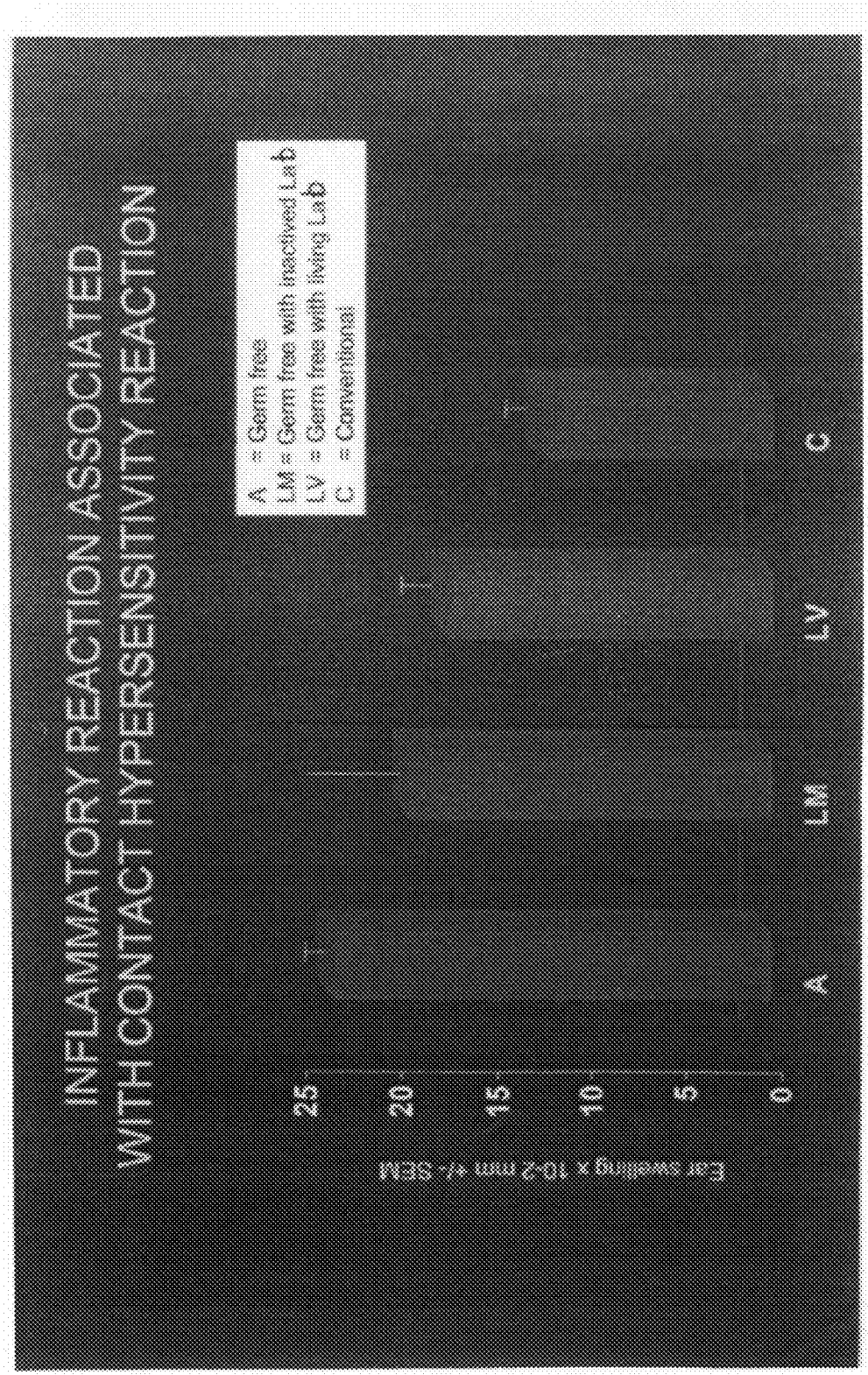
FIG. 1 shows the inflammatory reaction associated with a contact hypersensitivity reaction in the various mice models examined as determined by ear swelling.

The present invention provides for the first time that the gut flora composition may also have a beneficial effect on certain protective functions in regions of the bodies distant from the location at which the probiotic micro-organisms colonize the individual, namely the skin. Further, it has been shown that the probiotics may control in the skin divergent processes such as up-regulating the immune system during an immunosuppressive condition and at the same time down- regulating hyper-reactions, such as inflammatory or allergic reaction, such as eczema or atopic dermatitis. This holds especially true for elderly individuals, who normally have a reduced immunocapacity.

According to a preferred embodiment the probiotics to be included into the carrier are selected from the group consisting of Lactic acid bacteria, in particular Lactobacilli and/or Bifidobacteria and are more preferably *Lactobacillus johnsonii*, *Lactobacillus reuteri*, *Lactobacillus rhamnosus*, *Lactobacillus paracasei*, *Lactobacillus casei* or *Bifidobacterium bifidum*, *B. breve*, *B. animalis*, *B. infantis*, *B. dolescentis B. pseudocatenulatum*. Since due to their distinct oxygen requirement Lactobacilli and Bifidobacteria colonize the gut at different locations a mixture thereof may be used so as to provide a broad coverage.

According to a most preferred embodiment, the strains used are *Lactobacillus johnsonii* (La1) and *Lactobacillus paracasei* (ST11) deposited under the Budapest Treaty with the Institute Pasteur (28 rue du Docteur Roux, F-75724 Paris Cedex 15, France) on Jun. 30, 1992 and Jan. 12. 1999, respectively, under the deposit no. CNCM I-1225 and the deposit no. CNCM I-2116, respectively.

The carrier may be any food or pharmaceutical product, or a cosmetic product for oral or topical application, wherein the probiotic microorganism or a culture supernatant thereof may be included. Examples for food or pharmaceutical carriers are milk, yogurt, curd, cheese, fermented milks, milk based fermented products, ice-creams, fermented cereal based products, milk based powders, infant formulae or pet food, or tablets, liquid bacterial suspensions, dried oral supplement, wet oral supplement, dry tube-feeding or wet tube-feeding. For cosmetic products lotions, shampoos, creams, such as moisturising creams, sun-screens, after-sun creams or anti-aging creams, and/or ointments are envisaged, wherein the micro-organism may be included in a live form, semi-active or in deactivated form, e.g. as a lyophilized powder. Also culture supernatants of the micro-organisms may be included in the cosmetic products, optionally in concentrated form.

It will be appreciated that when administered to an individual as a micro-organism the probiotic's balancing activity will be dose dependant. Thus, it is envisaged to include as many as from $10^5$ to $10^{12}$ organisms/g product, which organisms may be alive or dead. When using a supernatant of a probiotic's culture the supernatant may be used as such or may subjected to one or more purification steps prior to inclusion into the product, so as to concentrate or isolate the active ingredient(s)/metabolite(s). Methods and techniques for purifying compounds and detecting the activity thereof in the fractions obtained are well known to the skilled person.

Though the present invention applies to all living beings, such as humans and animals, in particular pets, the probiotics are preferably used for elderly individuals, that generally have a reduced immuno-capacity.

During the far-reaching experimentation leading to the present invention a germ-free animal model was utilized focusing on microflora associated characteristics (MAC) vs. germfree animal characteristics (GAC), which characteristics are deemed to be of considerable value, particularly in allergic/inflammatory diseases with skin manifestations.

The following examples further illustrate the invention without limiting it thereto.

EXAMPLE 1

Balancing Hypersensitivity Reactions

In this experiment the activity of probiotics (dead or alive) on the skin's immune system under a chemical stress situation was evaluated. In this respect, animals were sensitized with a chemical compound (dinitrochlorobenzene) and the effect of such a (chemical) stress situation in axenic animals was compared to the effect in animals, the gut of which contained probiotics only. The level of a hypersensitivity reaction developed against DNCB was evaluated by several parameters (see below).

For the experiments male mice C3H (LPS+), germ free and supplied by the Research Center Orleans (CNRS Orléans, France) were assembled in four groups of eight mice each. The groups reflected different statuses of the gut and were designated "C" (group with a Conventional (normal) microflora), "LV" (group with a microflora consisting of LiVing Lactic acid bacteria only), "LD" (group fed with dead probiotics (*Lactobacillus* Dead) and "A" (germ free (Axenic) mice); all groups were maintained in isolated cages with group C being maintained under normal conditions.

The probiotic administered to the mice was the lactic acid bacterium ST11 (obtainable from the Institute Pasteur under the accession no. CNCM I-2116) which was given in a live form in a solution of $10^8$ cfu/ml (cfu=colony forming unit), or used dead or inactivated by irradiation in a solution of 2.1 g/25 ml in water when forced feeding was applied or in water at 3.3 g/l (below).

To obtain mice having a microflora essentially consisting of live lactic acid bacteria only, the germ free animals (supra) were force-fed twice on day 7 and day 8 with 0.5 ml of a solution containing $10^8$ cfu/ml each (group LV). Alternatively, in order to obtain mice having a gut microflora with the probiotic strain, inactivated by irradiation, the germ free animals were force-fed from day 36 to day 38, from day 41 to day 45, from day 48 to day 49 and from day 52 with 0.2 ml of a solution containing 2.1 g/25 ml inactivated microorganisms each day indicated. Staring from day 55 the above solution was replaced by a solution containing 3.3 g/l inactivated micro-organisms, which solution was provided until the end of experiment in drinking water (group LD). To obtain a conventional (normal) gut-microflora, the germ free animals were transferred three days after arrival into a common animal cage with normal feeding so as to develop a normal microflora. All the animals in groups A, LV and LD were examined on a regular basis for their fecal microbial composition, to ensure the maintenance of their specific gut status.

The animals in the different groups were sensibilized by topically applying on each flank 50 µl of 1% dinitrochlorobenzene (DNCB) on day 45 and 50, respectively. Five days after the last sensitization the animals were challenged on three consecutive days (on day 55, day 56 and day 57) by applying on the right ear 25 µl of 1% DNCB and on the left ear 25 µl of the carrier (olive oil) for all mice groups.

On day 58 the effect of the hypersensitivity reaction brought about by the above treatment with DNCB was examined. In this respect, the thickness of the right and left ears of each of the animals was measured on day 58 and the difference in the thickness between the two ears of the same animal has been calculated. The results are shown in FIG. 1 and are summarized in table I below:

TABLE 1

| Group | $\Delta$ ear thickness $10^{-2}$ mm ± s/$\sqrt{n}$ |
|---|---|
| A | 22.9 ± 2.2 |
| LD | 19.0 ± 3.6 |
| LV | 17.0 ± 3.3 |
| C | 12.1 ± 2.8 |

From the above it becomes evident that a hypersensitivity reaction as measured according to the ear thickness increases in the order

C<LV<LD<A

From these results, it can be concluded that a conventional intestinal flora permits a regulation of the inflammation as compared to mice lacking such a microflora. In addition, it may be seen that the implementation of the probiotic microorganism ST11 alone causes a reduction of the inflammation caused by DNCB, i.e. a tendency to reduce the edema of the ears of the animal exclusively with a lactic gut flora This finding is surprising, since the gut normally consists of an assembly of different micro-organisms, that all fulfil different tasks.

Moreover, in order to obtain biochemical data on immunological relevant responses on the molecular level to the stress situation cryo-sections of the right ear were prepared and examined for the level of ICAM-1 and TGF-β. ICAM-1 is a pro-inflammatory marker while TGF-β is an anti-inflammatory marker. Consequently, it is expected that the stress condition induced will result in the ICAM-1 level being high and the TGF-β level being low.

For the experiments the rat anti-mouse ICAM-1 antibody (clone KAT-1) at 1/25 (Caltag Laboratories, CA, USA) was used, then rabbit ant-rat FITC at 1/700 (Dako, Ca, USA). For the determination of TGF-β rabbit anti-human/mouse TGF-β (V) at 1/20 (Santa Cruz Biotechnology, Ca, USA), was utilized, then swine anti-rabbit-FITC at 1/1000 (Dako, Ca, USA).

Figure 2:
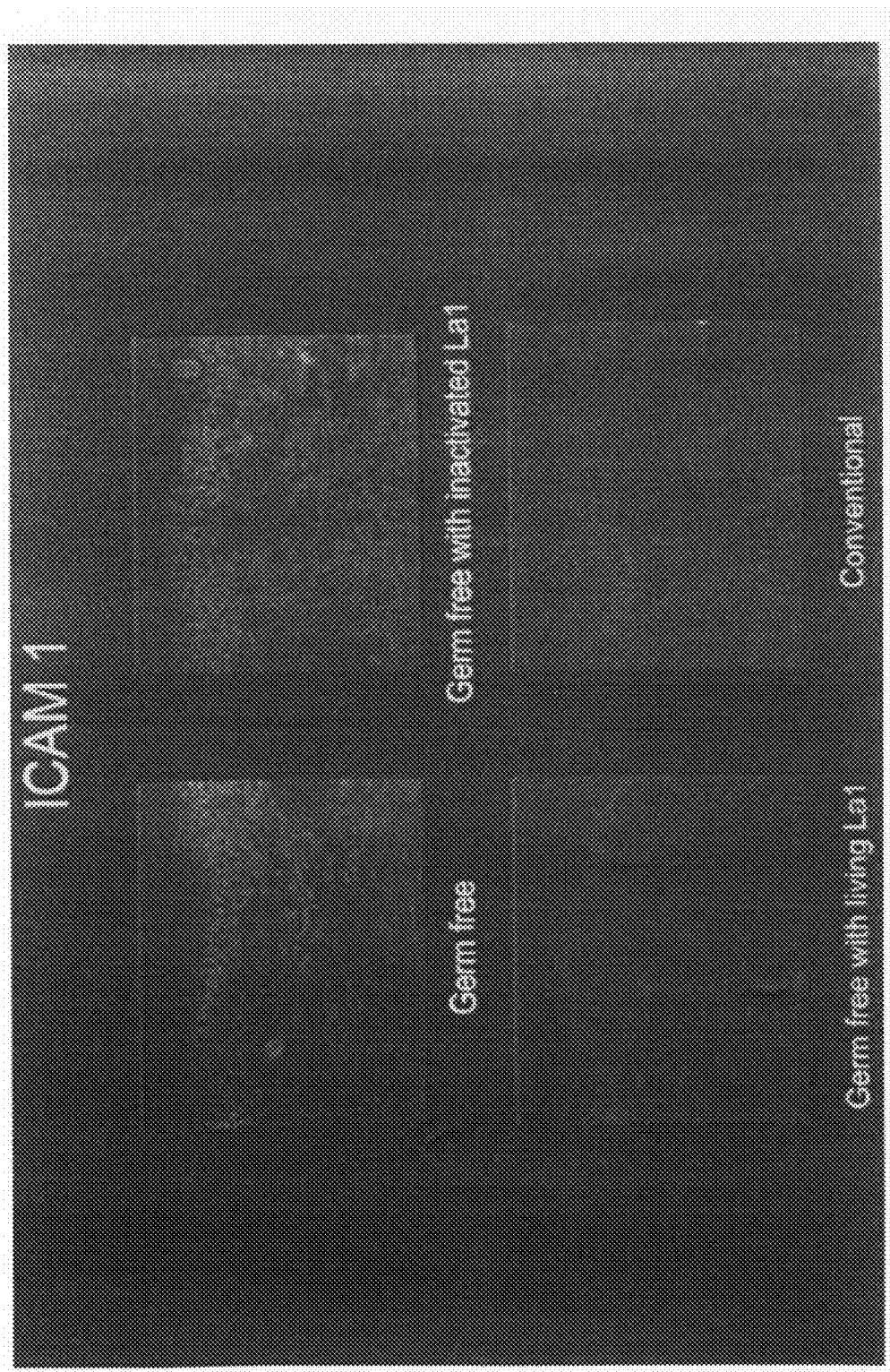
FIG. 2 shows the results obtained with an antibody against ICAM-1 in the various animal models indicating.

As may be seen from FIG. 2, in axenic animals a high level of the inflammatory cytokine ICAM-1 could be detected, while in animals treated with the living probiotic a decreased level of ICAM-1 could be observed, comparable to that found in animals having a conventional, i.e. normal microflora. Also animals treated with inactivated probiotic showed a decreased level of ICAM-1. According to this finding the following order may be set up

C=LV>LD>A

Again, based on the finding relating to this inflammatory marker animals having a gut microflora consisting of the lactic acid bacterium alone showed the same low level of ICAM-1 as did mice having a conventional microflora.

Figure 3:
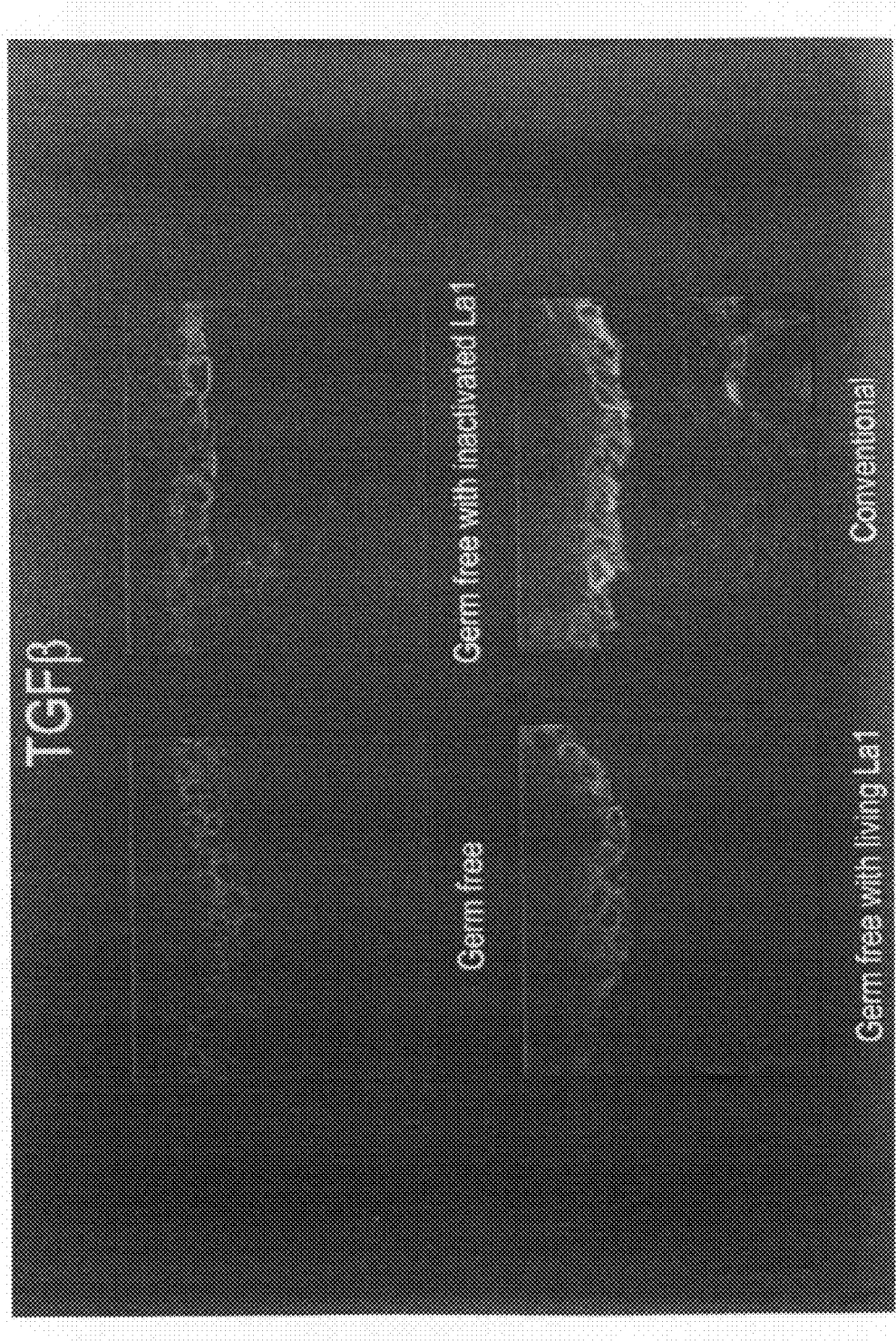
FIG. 3 shows the level of TGF-$\beta$ in the various animal models tested.

In contrast thereto, FIG. 3 shows that the level of the anti-inflammatory marker TGF-β was decreased in axenic animals as compared to animals having a conventional microflora. Yet, animals having a microflora with the living clearly showed an increased level of TGF-β as compared to axenic animals. The order to be set up for this marker is

C>LV>LD>A

In addition, skin samples were taken from the back of the mice and subjected to an extraction procedure according to the method described in Peguet et al., Br. J. Dermatol. 133 (1995), 661, which document is incorporated herein by way of reference. After taking skin samples, they were transferred on ice into an extraction buffer 10 mM Tris HCl, pH 7.4; 2 mM MgCl; 150 mM NaCl; 1% Triton X100; 2 mM PMSF) and subjected to an ultrasonication treatment. Also serum samples were taken from the animals. The serum samples and skin extracts were examined for their IL-10 level.

For performing the experiments the ultrasensitive ELISA test Cytoscreen® from Biosource International, CA, USA was used. The amount of IL-10 was calculated according to a standard curve (0.625 to 80 pg/ml)

Figure 4:
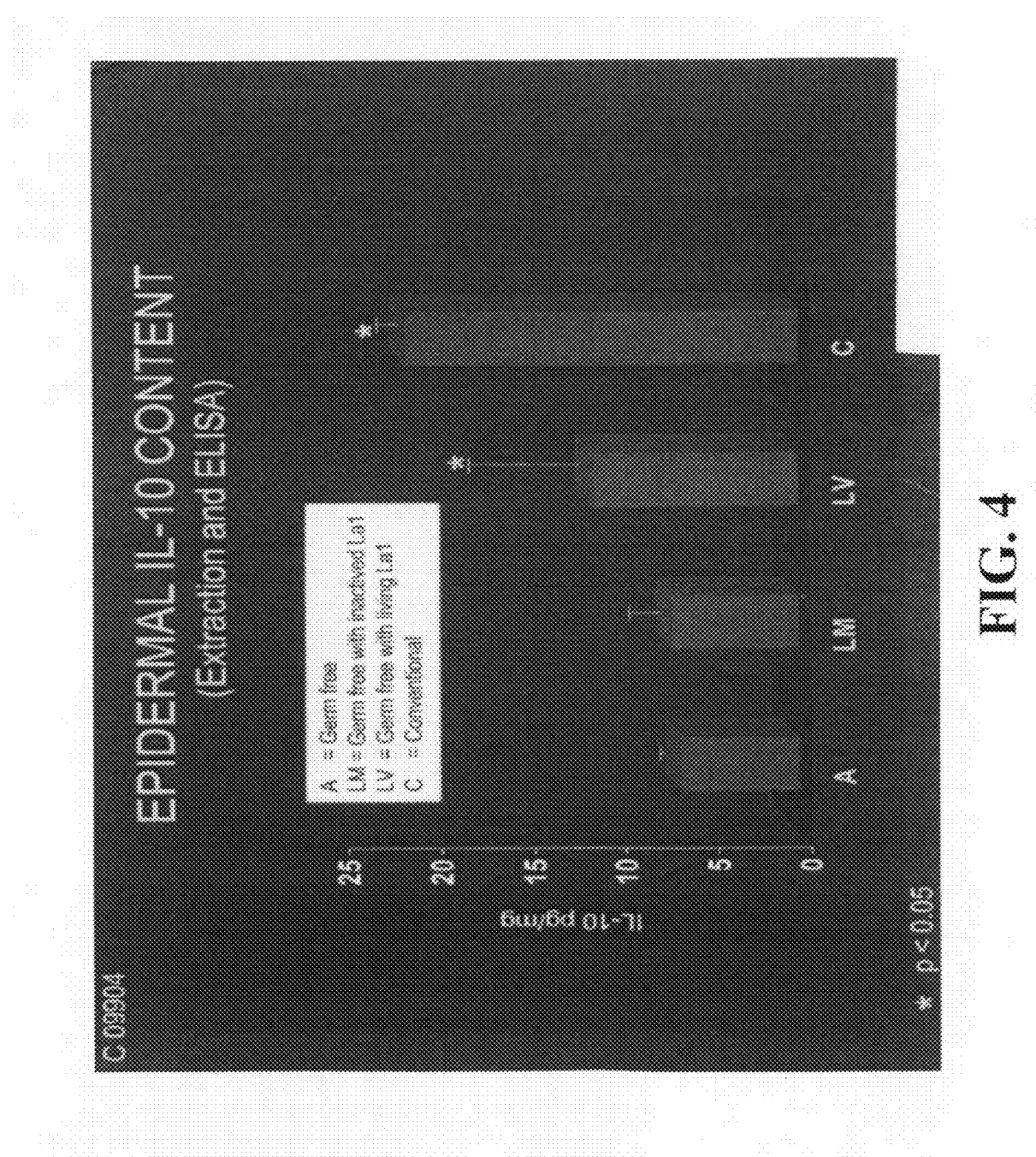
FIG. 4 shows the epidermal IL-10 level in the various animal models tested.

For the extracts the results are reported according to the amount of proteins (Lowry method) contained in the extracts based on the total amount of cellular material. The results are expressed in pg IL-10 and shown in FIG. 4 and table II below.

TABLE II

| Groups | IL-10 pg/mg |
|---|---|
| A | 6.3 ± 2.2 |
| LD | 6.8 ± 1.7 |
| LV | 11.1 ± 1.8 |
| C | 21.2 ± 3.2 |

As may be clearly seen, the amount of IL10 is the highest in mice having a conventional microflora with the group treated wit live probiotic being superior to axenic mice. The following order may be set up:

C>LV>LD>A

Based on the finding in this experiment it may clearly be seen that the different parameters tested (TGF-β, ICAM-1, IL10) confirm the results found with the difference in ear thickness, i.e. a regulation of inflammatory reactions by implanting a lactobacillus microflora.

EXAMPLE 2

In this experiment the UV-light induced suppression of the immune system in the skin, as perceptible by an diminished development of a hypersensitivity reaction, was used to investigate the potential of probiotics to essentially restore the immune system's capability to respond to stress situations, such as being exposed to an allergenic substance, in a normal way.

Three test groups of animals were set up. The first group of animals was treated with a compound known to elicit hypersensitive reactions, dinitrofluorobenzene (DNFB), and the reaction of the skin's immune system thereto was determined. The second group was subjected to UV irradiation prior to being exposed to the compound above and the effect of said exposure on the immune reaction under these conditions was assessed. The third group received probiotics in living or inactivated form, or a culture supernatant thereof, and was exposed to UV-light. In this group the effect of the probiotics on the restoration of the immune response was evaluated. For performing the experiment female Skh1/hr mice (obtained from Charles River Laboratories (France)) aged between 8 and 10 weeks were used. As probiotics administered to the different groups the products listed in table III were utilized:

TABLE III

| | |
|---|---|
| Product 1 | culture medium |
| Product 2 | live La1 (obtainable from Institute Pasteur, CNCM I-1225) |
| Product 3 | inactivated La1 |
| Product 4 | supernatant of La1 |
| Product 5 | live ST11 (obtainable from Institute Pasteur, CNCM I-2116) |
| Product 6 | inactivated ST11 |
| Product 7 | culture supernatant of ST11 |

The probiotic samples were provided in frozen aliquots of 1.5 ml containing $10^9$ cfu/ml. As a control the culture medium (product 1) was utilized.

32 groups of 10 mice each were assembled. Animals were fed with the respective products starting 10 days before day 0, the day of exposing the animals to UV-light, and continuing such feeding until day 12, on which the challenge with DNFB took place. Consequently, the products were fed to the animals for 23 days in total. The products 1 to 7 (supra) were force-fed to groups 5 to 32 at a dosage of 100 μl/animal corresponding to about $10^8$ cfu/animal/day. Table IV lists the products and the groups receiving them.

TABLE IV

| | |
|---|---|
| Product 1 (culture medium) | groups 5-8 |
| Product 2 (live La1) | groups 9-12 |
| Product 3 (inactivated La1) | groups 13-16 |
| Product 4 (supernatant of La1) | groups 17-20 |
| Product 5 (live ST11) | groups 21-24 |
| Product 6 (inactivated ST11) | groups 25-28 |
| Product 7 (supernatant of ST11) | groups 29-32 |

On day 0 the mice were lightly anestesized with isofluorane/oxygen and subsequently irradiated by means of a sun-simulator containing a Xenon 1000 W (Oriel) lamp including a dichroic mirror (Oriel, Stafford, USA) equipped with a WG 320/1 mm thick filter and a UG11 filter/1 mm thick (Schott). This filtered source provided a simulated solar US spectrum (290-400 nm) that almost eliminated all visible and infrared radiation. The amount of radiation as determined by means of radiometer ARCC 1600 (Osram) was 1.95 mW/cm$^2$ at UVB and 9.35 mW/cm$^2$ at UVA. The spectrum applied conforms to the norm of according to SPF COLIPA Mice of the groups 3, 4, 7, 8, 9, 11, 12, 15, 16, 19, 20, 23, 24, 27, 28, 31, 32 were irradiated, with the ears being protected (day 0). They received a singular dose of 2.5 MED.

On day 5 and day 6 a hypersensitivity reaction was induced by topically applying on the abdomen 50 μl acetone (groups 1, 3, 5, 7, 9, 11, 13, 15, 17, 19, 21, 23, 25, 27, 29, 31) and DNFB (0.3% in acetone; groups 2, 4, 6, 8, 10, 12, 14, 16, 18, 20, 22, 24, 26, 28, 30, 32), respectively.

On day 12, 5 µl of a 0.2% DNFB solution in acetone was applied on the right ear of all mice. The animals were weighed at the beginning (day 0) and at the end of the tests (day 13).

The evaluation of the inflammatory reaction was performed 24 hours after exposure to UV-light, i.e. on day 1. Two parameters were assessed, namely the intensity of the erythema on the back by means of clinically determining the erythema and the edema, with calculating the means of each group and the increase of the thickness of the skin at the back, with calculating the means of the non-irradiated and the irradiated animals.

Figure 5:
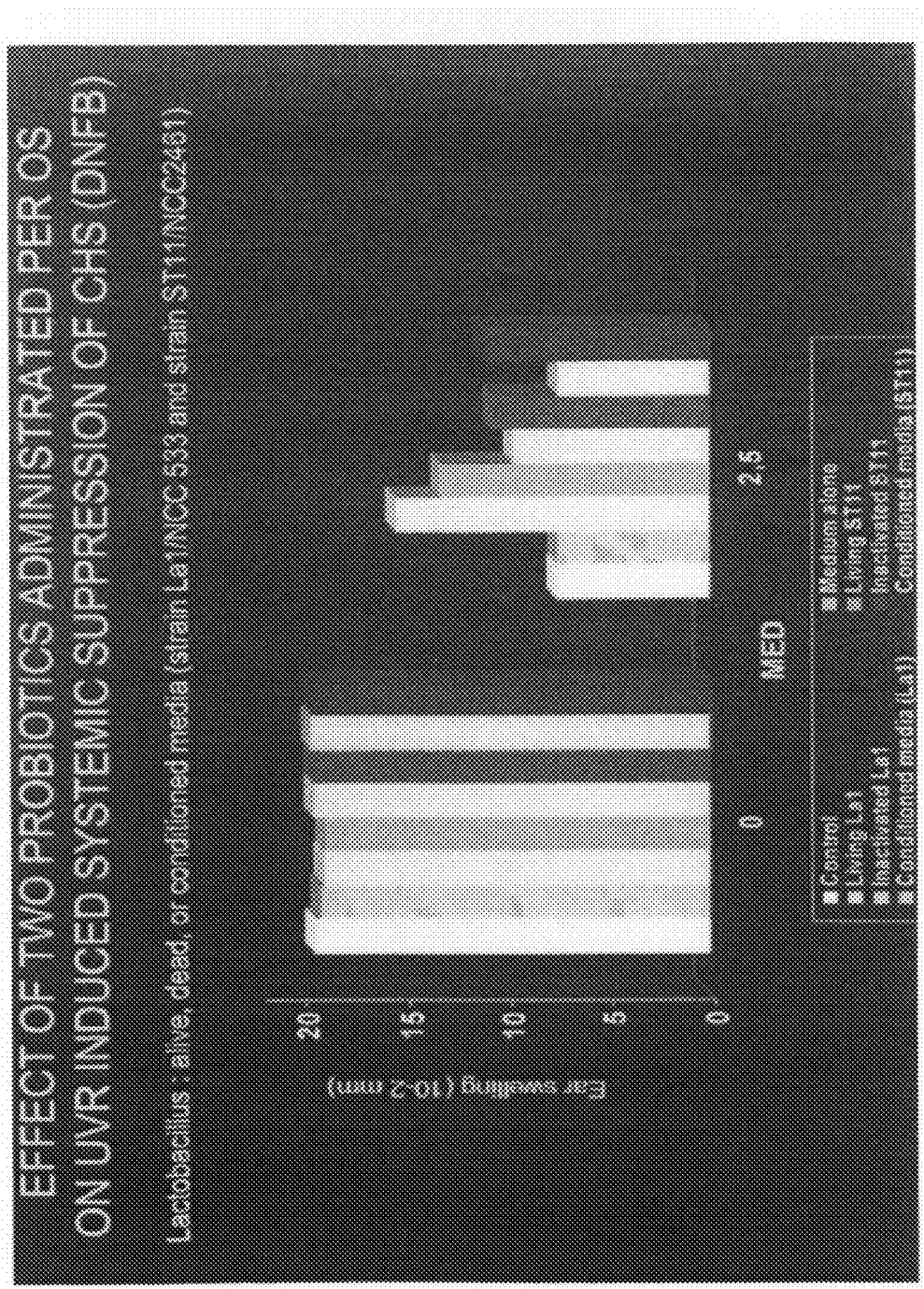
FIG. 5 shows the effects of probiotics on an UV irradiation induced suppression of the immune system shown according to a contact hypersensitivity reaction as determined by ear swelling.
Figure 6:
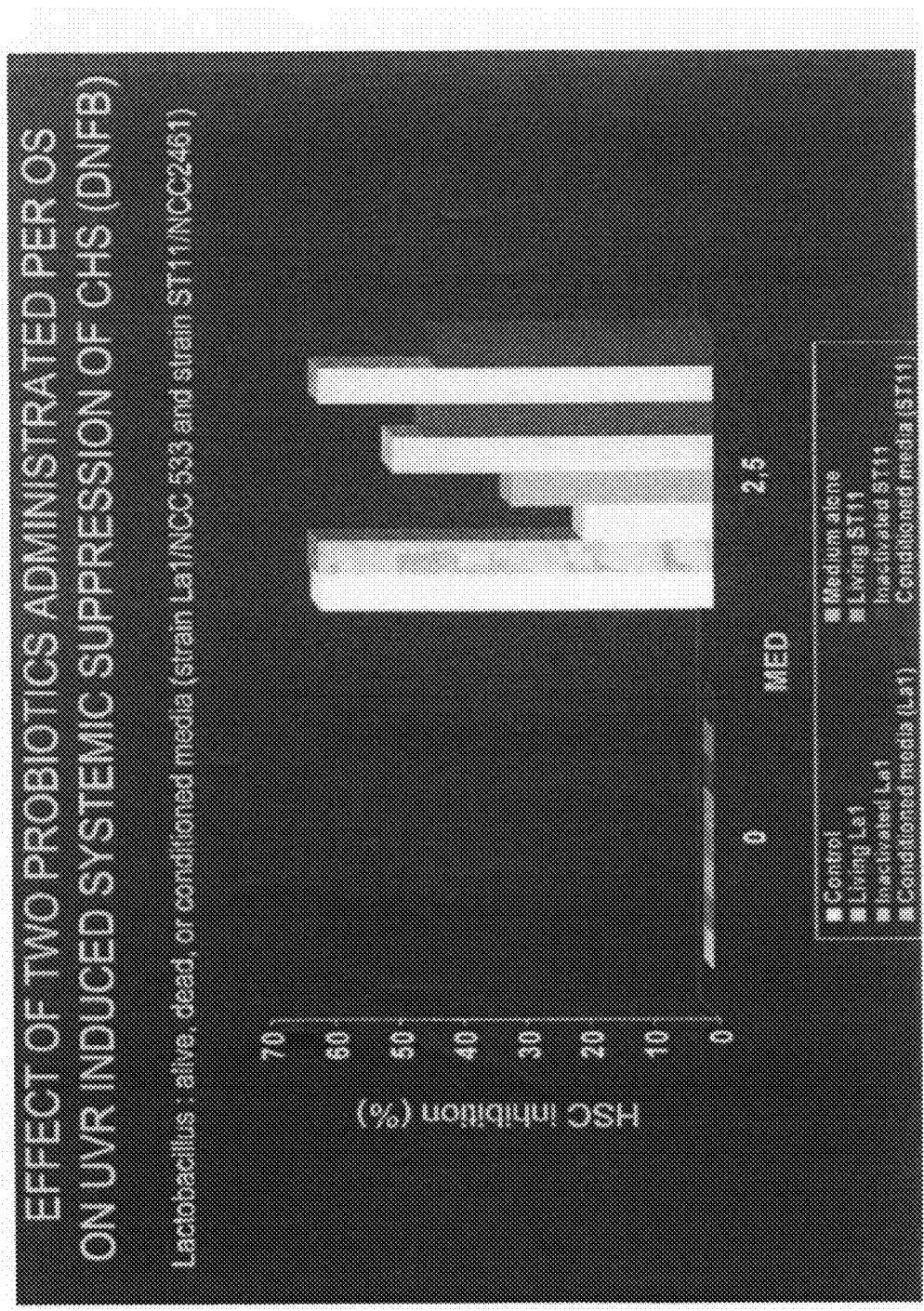
FIG. 6 shows the effects of probiotics on an UV irradiation induced suppression of the immune system shown as % CHS inhibition.

The determination of the skin thickness at the right and the left ear was performed on day 13. The difference of the skin thickness of the ears of the same animal and the medium value of each group was calculated. The results shown in the table V below are graphically depicted in the FIGS. 5 and 6.

TABLE V

Hypersensibility reaction as determined by the ear thickness

| | Irradiation MED | Treatment | Induction | Δ ear thickness épaisseur $10^{-2}$ mm ± s/√n | % Inhibition of HSC by irradiation |
|---|---|---|---|---|---|
| 1 | 0 | — | Acetone | 1.1 ± 0.2 | |
| 2 | 0 | — | DNFB 0.3% | 19.3 ± 0.4 | |
| 3 | 2.5 | — | Acetone | 1.0 ± 0.2 | |
| 4 | 2.5 | — | DNFB 0.3% | 7.5 ± 0.2 | 61.1 |
| 5 | 0 | Culture medium | Acetone | 1.0 ± 0.1 | |
| 6 | 0 | Culture medium | DNFB 0.3% | 19.0 ± 0.2 | 0 |
| 7 | 2.5 | Culture medium | Acetone | 1.0 ± 0.2 | |
| 8 | 2.5 | Culture medium | DNFB 0.3% | 7.4 ± 0.1 | 61.6 |
| 9 | 0 | La1 alive | Acetone | 1.1 ± 0.3 | |
| 10 | 0 | La1 alive | DNFB 0.3% | 18.9 ± 0.2 | 0 |
| 11 | 2.5 | La1 alive | Acetone | 1.3 ± 0.2 | |
| 12 | 2.5 | La1 alive | DNFB 0.3% | 15.4 ± 0.2 | 20.2 |
| 13 | 0 | La1 dead | Acetone | 1.3 ± 0.2 | |
| 14 | 0 | La1 dead | DNFB 0.3% | 19.4 ± 0.3 | 0 |
| 15 | 2.5 | La1 dead | Acetone | 1.4 ± 0.1 | |
| 16 | 2.5 | La1 dead | DNFB 0.3% | 9.6 ± 0.3 | 50.3 |
| 17 | 0 | Culture supernatant of La1 | Acetone | 1.1 ± 0.2 | |
| 18 | 0 | Culture supernatant of La1 | DNFB 0.3% | 19.5 ± 0.4 | 0 |
| 19 | 2.5 | Culture supernatant of La1 | Acetone | 1.1 ± 0.3 | |
| 20 | 2.5 | Culture supernatant of La1 | DNFB 0.3% | 7.4 ± 0.1 | 61.7 |
| 21 | 0 | ST11 alive | Acetone | 0.6 ± 0.2 | |
| 22 | 0 | ST11 alive | DNFB 0.3% | 18.8 ± 0.2 | 0 |
| 23 | 2.5 | ST11 alive | Acetone | 1.1 ± 0.2 | |
| 24 | 2.5 | ST11 alive | DNFB 0.3% | 13.2 ± 0.3 | 31.6 |
| 25 | 0 | ST11 dead | Acetone | 1.4 ± 0.2 | |
| 26 | 0 | ST11 dead | DNFB 0.3% | 19.4 ± 0.4 | 0 |
| 27 | 2.5 | ST11 dead | Acetone | 1.1 ± 0.3 | |
| 28 | 2.5 | ST11 dead | DNFB 0.3% | 10.6 ± 0.3 | 45.1 |
| 29 | 0 | Culture supernatant of ST11 | Acetone | 1.0 ± 0.2 | |
| 30 | 0 | Culture supernatant of ST11 | DNFB 0.3% | 19.3 ± 0.4 | 0 |
| 31 | 2.5 | Culture supernatant of ST11 | Acetone | 1.2 ± 0.2 | |
| 32 | 2.5 | Culture supernatant of ST11 | DNFB 0.3% | 11.0 ± 0.2 | 43 |

As expected, exposure to UV-light systemically suppressed a hypersensitivity reaction to DNFB in mice receiving no treatment at all and in control mice, receiving the culture medium alone. Those mice receiving live probiotic micro-organisms or culture supernatants thereof (conditioned media) clearly showed a recovery of the immune system and exhibited a hypersensitivity reaction against DNFB. From these findings it becomes obvious that probiotics and to some extent also their metabolites, present in the culture supernatant, are clearly capable to modulate the immune system in an UV-light induced suppressed condition such that the immune response is essentially restored.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A method for improving an individual's skin disorder associated with an unbalanced immune condition caused by a stress condition associated with ultraviolet irradiation that leads to a suppression or an over-stimulation of an immune system, the method comprising the steps of administering a composition including a carrier and a probiotic lactic acid bacteria or a culture supernatant thereof having the capability to interact with the immune system, wherein the lactic acid bacteria comprises a bacterial strain identified by a deposit number selected from the group consisting of CNCM I-1225 and CNCM I-2116 and combinations thereof.

2. The method according to claim 1 wherein the individual is suffering inflammatory and irritant effects caused by a stress condition.

3. The method according to claim 2 wherein the stress condition is chosen from the group consisting of a physical, a chemical and a biological stress condition.

4. The method according to claim 1 wherein the carrier is selected from the group consisting of milk, yogurt, curd, cheese, fermented milks, milk based fermented products, ice-creams, fermented cereal based products, milk based powders, infant formulae, tablets, liquid bacterial suspensions, dried oral supplement, wet oral supplement, dry tube feeding or wet tube feeding, pet food or lotions, shampoos, creams, and ointments.

5. The method according to claim 1 wherein the probiotic lactic acid bacteria is present in the carrier in an amount of from about $10^5$ to about $10^{12}$ cfu/g carrier.

6. The method according to claim 1 wherein the individual is a human being.

7. The method according to claim 1 wherein the individual is a pet.

8. The method of claim 1 wherein the probiotic lactic acid is part of a culture supernatant.

* * * * *